United States Patent
Watanabe

(10) Patent No.: US 11,553,878 B2
(45) Date of Patent: Jan. 17, 2023

(54) BLOOD-VESSEL RECOGNIZING METHOD AND BLOOD-VESSEL RECOGNIZING DEVICE

(71) Applicant: OLYMPUS CORPORATION, Tokyo (JP)

(72) Inventor: Takeshi Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 470 days.

(21) Appl. No.: 16/775,534

(22) Filed: Jan. 29, 2020

(65) Prior Publication Data
US 2020/0170569 A1 Jun. 4, 2020

Related U.S. Application Data

(63) Continuation of application No. PCT/JP2017/029334, filed on Aug. 15, 2017.

(51) Int. Cl.
*A61B 5/00* (2006.01)
*A61B 5/026* (2006.01)
(Continued)

(52) U.S. Cl.
CPC ............ *A61B 5/489* (2013.01); *A61B 5/0261* (2013.01); *A61B 5/1075* (2013.01);
(Continued)

(58) Field of Classification Search
CPC ..... A61B 5/489; A61B 5/0261; A61B 5/1075; A61B 5/7203; A61B 5/7282;
(Continued)

(56) References Cited

U.S. PATENT DOCUMENTS 5,928,153 A * 7/1999 Chiang .................... A61B 8/06
600/455
2003/0201935 A1* 10/2003 King ...................... G01S 19/29
342/357.62
(Continued)

FOREIGN PATENT DOCUMENTS

EP 1992270 A1 11/2008
EP 3251582 A1 12/2017
(Continued)

OTHER PUBLICATIONS

International Search Report dated Oct. 31, 2017 issued in PCT/JP2017/029334.

*Primary Examiner* — Nasim N Nirjhar
(74) *Attorney, Agent, or Firm* — Scully, Scott, Murphy & Presser, P.C.

(57) ABSTRACT

A blood-vessel recognizing method for recognizing blood vessels present in biological tissue, the method including: obtaining real-time Doppler spectra on the basis of time waveforms data of intensities of scattered light generated in the biological tissue due to irradiation with laser light; calculating average frequencies of the real-time Doppler spectra; correcting the calculated average frequencies on the basis of peak intensities of the real-time Doppler spectra; and determining whether or not blood vessels are present in regions of the biological tissue irradiated with the laser light on the basis of the corrected average frequencies.

10 Claims, 12 Drawing Sheets

(51) Int. Cl.
*A61B 5/107* (2006.01)
*A61B 90/30* (2016.01)

(52) U.S. Cl.
CPC .......... *A61B 5/7203* (2013.01); *A61B 5/7282* (2013.01); *A61B 2090/306* (2016.02)

(58) Field of Classification Search
CPC ... A61B 2090/306; A61B 1/00; A61B 5/7239; A61B 10/00
See application file for complete search history.

(56) References Cited

U.S. PATENT DOCUMENTS

| | | | |
|---|---|---|---|
| 2008/0306338 A1 | 12/2008 | Yamazaki et al. | |
| 2017/0258296 A1 | 9/2017 | Kaku | |
| 2017/0273668 A1* | 9/2017 | Matsumoto | A61B 8/5223 |
| 2017/0311877 A1* | 11/2017 | Watanabe | A61B 5/0075 |
| 2018/0008152 A1 | 1/2018 | Watanabe et al. | |
| 2018/0055372 A1 | 3/2018 | Watanabe et al. | |
| 2020/0077892 A1* | 3/2020 | Tran | A61B 5/6806 |

FOREIGN PATENT DOCUMENTS

| | | | | |
|---|---|---|---|---|
| JP | 2007-236415 A | 9/2007 | | |
| JP | 2016-144626 A | 8/2016 | | |
| WO | WO-2016117703 A1 * | 7/2016 | ............... | A61B 1/00 |
| WO | WO 2016/151787 A1 | 9/2016 | | |
| WO | WO 2016/170636 A1 | 10/2016 | | |
| WO | WO 2016/171238 A1 | 10/2016 | | |

\* cited by examiner

BLOOD-VESSEL RECOGNIZING METHOD AND BLOOD-VESSEL RECOGNIZING DEVICE

CROSS-REFERENCE TO RELATED APPLICATIONS

This is a continuation of International Application PCT/JP2017/029334 which is hereby incorporated by reference herein in its entirety.

TECHNICAL FIELD

The present invention relates to a blood-vessel recognizing method and a blood-vessel recognizing device.

BACKGROUND ART

In performing a surgical procedure on biological tissue, it is important that the surgeon accurately recognizes blood vessels in the interior of the biological tissue. Thus, there is a known device equipped with a function for recognizing blood vessels present in biological tissue (for example, see Patent Literatures 1 and 2). In Patent Literatures 1 and 2, blood vessels are extracted from an image on the basis of differences between the blood vessels and other regions in terms of light reflection or absorption, and the extracted blood vessels are emphasized in the image.

CITATION LIST

Patent Literature

{PTL 1} Japanese Unexamined Patent Application, Publication No. 2016-144626
{PTL 2} Japanese Unexamined Patent Application, Publication No. 2007-236415

SUMMARY OF INVENTION

One aspect of the present invention is a blood-vessel recognizing method for recognizing blood vessels present in biological tissue, the method including: obtaining real-time Doppler spectra on the basis of time waveforms data of intensities of scattered light generated in the biological tissue due to irradiation with laser light; calculating average frequencies of the real-time Doppler spectra; correcting the calculated average frequencies on the basis of peak intensities of the real-time Doppler spectra; and determining whether or not blood vessels are present in regions of the biological tissue irradiated with the laser light on the basis of the corrected average frequencies.

Another aspect of the present invention is a blood-vessel recognizing device including: an optical fiber that radiates laser light onto biological tissue; and one or more processors comprising hardware, wherein the one or more processors are configured to: acquire real-time Doppler spectra on the basis of time waveforms data of intensities of scattered light generated in the biological tissue due to the irradiation with the laser light; calculate average frequencies of the acquired real-time Doppler spectra; correct the calculated average frequencies on the basis of peak intensities of the real-time Doppler spectra; and determine whether or not blood vessels are present in regions of the biological tissue irradiated with the laser light on the basis of the corrected average frequencies.

DESCRIPTION OF EMBODIMENT

A blood-vessel recognizing device according to an embodiment of the present invention will be described below with reference to the drawings.

Figure 1:
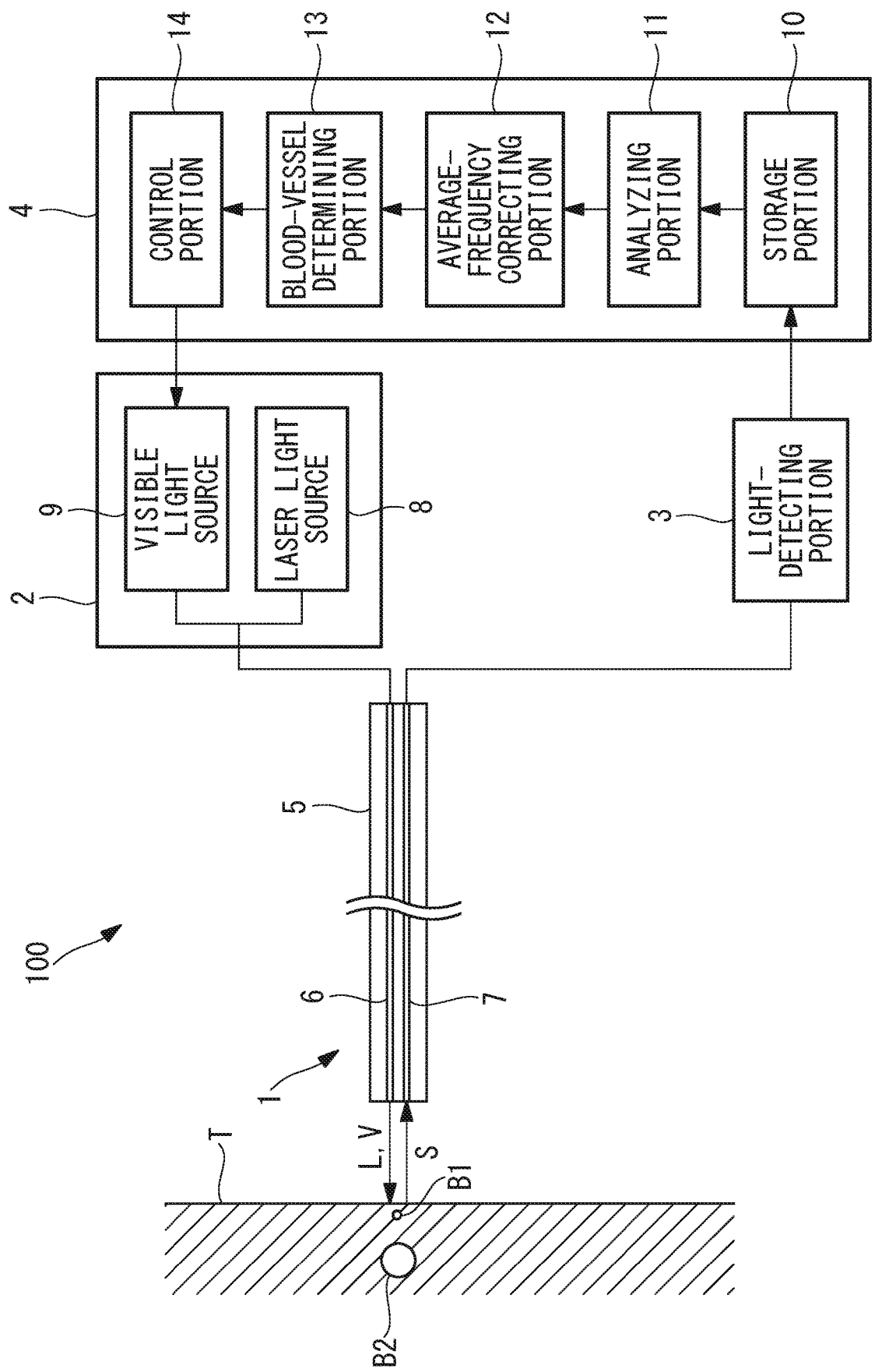
FIG. 1 is an overall configuration diagram of a blood-vessel recognizing device according to an embodiment of the present invention.

As shown in FIG. 1, a blood-vessel recognizing device 100 according to this embodiment comprises: a probe 1 that can be inserted into a living organism, that radiates laser light L toward tissue T in the living organism, and that receives scattered light S from the tissue T; a light-source unit 2 that supplies the probe 1 with the laser light L and visible light V; a light-detecting portion (spectrum acquisition portion) 3 that detects the scattered light S received by the probe 1; and a control device 4 that applies analytical processing to data for the scattered light S detected by the light-detecting portion 3 and that controls the light-source unit 2.

The probe 1 comprises: a long, thin probe body 5; and an irradiation optical fiber (laser-light radiating portion) 6 and a light-receiving optical fiber (spectrum acquisition portion) 7 that are provided in the probe body 5 along the longitudinal direction thereof.

The probe 1 may be a treatment device with which the tissue T is treated, such as a high-frequency scalpel. In this case, a working portion (not shown) for treating the tissue T is provided at a distal end of the probe body 5.

A distal end of the irradiation optical fiber 6 is disposed in the vicinity of the distal end of the probe body 5, and a base end of the irradiation optical fiber 6 is connected to the light-source unit 2. The laser light L and the visible light V supplied to the base end of the irradiation optical fiber 6 from the light-source unit 2 are emitted forward in the longitudinal direction of the probe body 5 from the distal end of the irradiation optical fiber 6.

A distal end of the light-receiving optical fiber 7 is disposed in the vicinity of the distal end of the probe body 5, and a base end of the light-receiving optical fiber 7 is connected to the light-detecting portion 3. The scattered light S of the laser light L scattered by the tissue T is received by the light-receiving optical fiber 7 and is guided to the light-detecting portion 3.

The light-source unit 2 comprises: a laser light source 8 that outputs the laser light L; a visible light source 9 that outputs the visible light V having a wavelength in the visible range; and an optical multiplexer (not shown) that combines the laser light L and the visible light V and makes the combined light enter the irradiation optical fiber 6.

The laser light source 8 outputs the laser light L in a wavelength range in which absorption by blood is low and in which the laser light L is allowed to reach a deep portion from a surface layer of the tissue T (for example, the near infrared region or the infrared region). The surface layer refers to a region between the surface of the tissue T and a depth of about several tens of micrometers to several hundreds of micrometers. The deep portion refers to a region that is deeper than several hundreds of micrometers from the surface of the tissue T (for example, a region at a depth that is equal to or greater than 3 mm from the surface of the tissue T). Many small blood vessels B1 are present in the surface layer, and many large blood vessels B2 (for example, blood vessels having diameters that are equal to greater than 2 mm) are present in the deep portion. Therefore, the scattered light S that is received by the light-receiving optical fiber 7 could contain scattered light S generated by the small blood vessels B1 and scattered light S generated by the large blood vessels B2.

It is preferable that the visible light source 9 be a laser light source. It is preferable that the color of the visible light V be a color that allows a surgeon to easily visually recognize the visible light V radiated onto the tissue T, for example, green or blue.

The light-detecting portion 3 comprises a photodetector such as a photodiode or a photomultiplier tube. The light-detecting portion 3 receives the scattered light S guided thereto by the light-receiving optical fiber 7 and converts the intensity of the received scattered light S to a digital value.

The obtained digital value is transmitted to a storage portion 10 (described later) in the control device 4.

The control device 4 comprises: the storage portion (spectrum acquisition portion) 10 that generates time waveforms by accumulating data about the intensities of the scattered light S detected by the light-detecting portion 3; an analyzing portion (average-frequency calculating portion) 11 that calculates an average frequency$<\omega>$ of real-time Doppler spectra Freal ($\omega$) by analyzing the time waveforms generated in the storage portion 10; an average-frequency correcting portion 12 that corrects the average frequency$<\omega>$; a blood-vessel determining portion 13 that determines the presence/absence of the large blood vessels B2 on the basis of the corrected average frequency$<\omega>_{cal}$; and a control portion 14 that controls the laser light source 8 and the visible light source 9.

The control device 4 is, for example, a computer, and comprises: a central processing unit (CPU); a main storage device such as a RAM; and an auxiliary storage device. The auxiliary storage device is a non-temporary storage medium, such as a hard disk drive, and stores programs for causing the CPU to execute processing (described later) performed by the analyzing portion 11, the average-frequency correcting portion 12, the blood-vessel determining portion 13, and the control portion 14. The processing performed by each of the portions 11, 12, 13, and 14 is realized as a result of the programs being loaded into the main storage device from the auxiliary storage device and the CPU executing the processing in accordance with the programs. Alternatively, the processing performed by each of the portions 11, 12, 13, and 14 may be realized by means of an FPGA (programmable logic device) or dedicated hardware such as an ASIC (application specific integrated circuit).

The storage portion 10 is formed from, for example, the main storage device or another type of storage. The storage portion 10 generates time-waveform data of the intensities of the scattered light S by time-sequentially storing the digital values received from the light-detecting portion 3.

Figure 2:
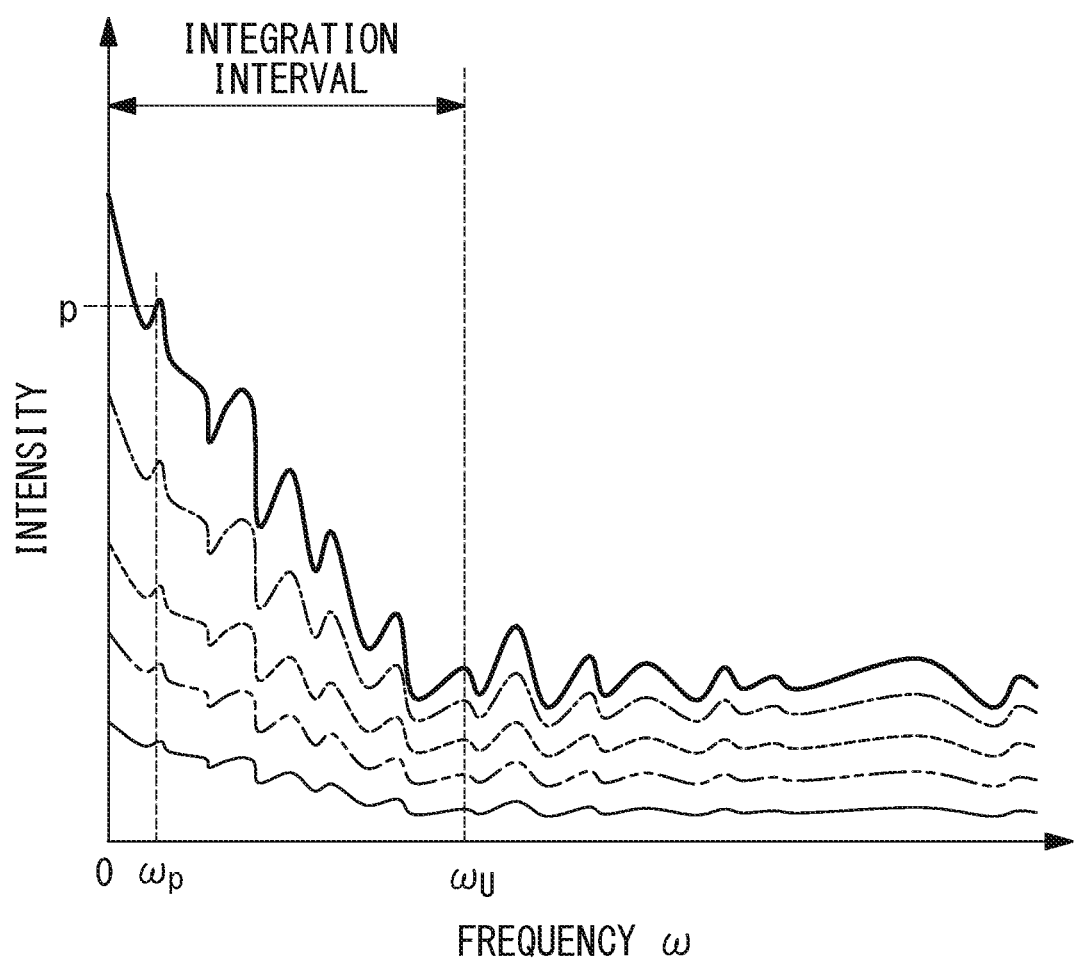
FIG. 2 is a diagram showing examples of real-time Doppler spectra calculated by an analyzing portion of the blood-vessel recognizing device in FIG. 1, and is a diagram for explaining the relationship between the depths of blood vessels and the intensities of the real-time Doppler spectra.

The analyzing portion 11 reads out the time waveform data from the storage portion 10 and obtains the real-time Doppler spectra Freal ($\omega$) by applying high-speed Fourier transformation to the time waveform data. As shown in FIG. 2, the real-time Doppler spectra Freal ($\omega$) are decay curves in which the intensities decrease toward the high-frequency side, and exhibit the intensities at frequencies $\omega$ in accordance with the blood-flow velocities in the blood vessels B1 and B2 that generate the scattered light S. Specifically, because the Doppler shift of the scattered light S caused by blood decreases with a decrease in the blood-flow velocity, intensity distributions of the real-time Doppler spectra Freal ($\omega$) are skewed toward the low-frequency side. On the other hand, because the Doppler shift of the scattered light S caused by blood increases with an increase in the blood-flow velocity, the intensity distributions of the real-time Doppler spectra Freal ($\omega$) spread out toward the high-frequency side. The blood-flow velocity is known to be substantially proportional to the size of the blood vessel. Therefore, it is possible to estimate the sizes of the blood vessels B1 and B2 from the average frequencies$<\omega>$ of the real-time Doppler spectra Freal ($\omega$).

Next, the analyzing portion 11 sets an integration interval for calculating the average frequencies$<\omega>$. As shown in FIG. 2, the integration interval is set to be an interval $0 \leq \omega \leq \omega_U$ on the basis of the spectral shapes of the real-time Doppler spectra Freal ($\omega$) so as to exclude the high-frequency range in which the real-time Doppler spectra Freal (ω) decay to a background level, and thus the spectral intensities become the lowest.

Next, the analyzing portion 11 calculates the average frequencies<ω> in the integration interval $0 \leq \omega \leq \omega_U$ on the basis of equation (1) below.

$$\langle \omega \rangle = \frac{\int_0^{\omega_U} \omega \times Freal(\omega) d\omega}{\int_0^{\omega_U} \omega d\omega} \quad (1)$$

FIG. 2 shows examples of the real-time Doppler spectra Freal (ω) obtained from blood vessels at different depths in biological tissue at the same blood-flow velocity.

Ideally, the average frequencies<ω> have a one-to-one correspondence with the blood-flow velocities. However, in reality, different average frequencies<ω> could be calculated even if the blood-flow velocities are the same. This is because, due to scattering or the like of the laser light L and scattered light S caused by the tissue T, the intensities of the scattered light S detected by the light-detecting portion 3 decrease with an increase in the depths at which the blood vessels B1 and B2 are located, as shown in FIG. 2, the intensities of the real-time Doppler spectra Freal (ω) decrease as a whole, thus decreasing the average frequencies<ω>. Furthermore, as the intensities of the real-time Doppler spectra Freal (ω) approach the background level, the calculation precision of the average frequencies<ω> decreases as a result of being more strongly influenced by noise.

Figure 3A:
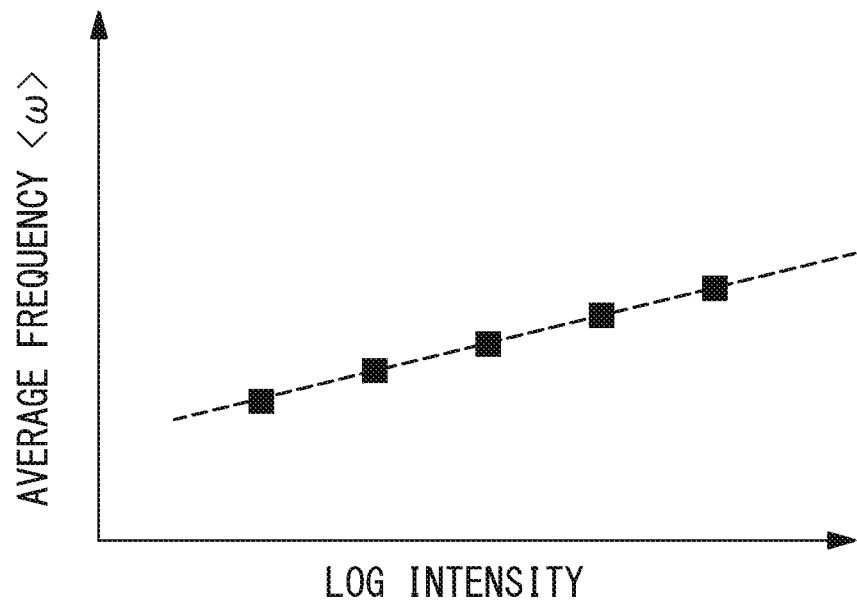
FIG. 3A is graph showing the relationship between average frequencies (vertical axis) calculated in an integration interval $0 \leq \omega \leq \omega_U$ and the intensities (horizontal axis) of the real-time Doppler spectra at the average frequencies.
Figure 3B:
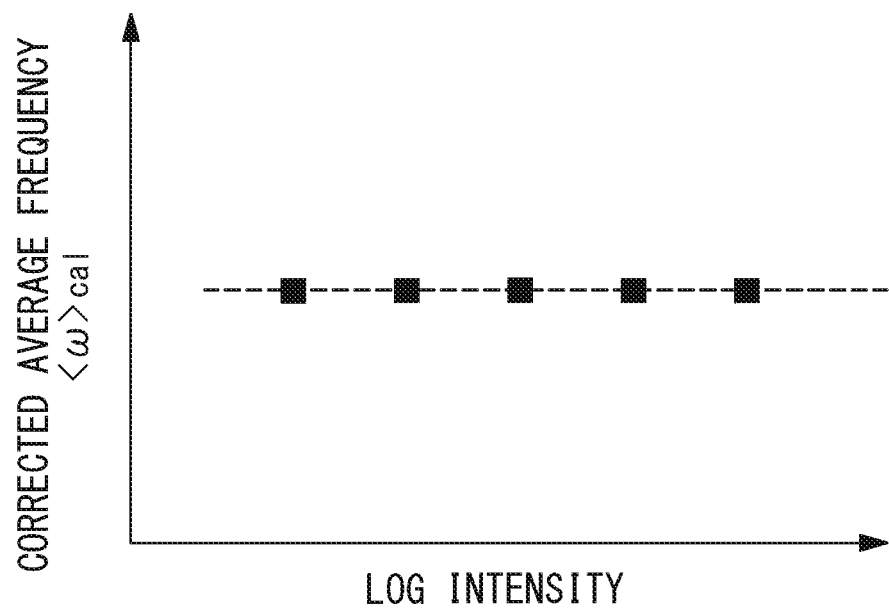
FIG. 3B is a graph showing the relationship between corrected average frequencies (vertical axis) and the intensities (horizontal axis) of the real-time Doppler spectra at the average frequencies.
Figure 3C:
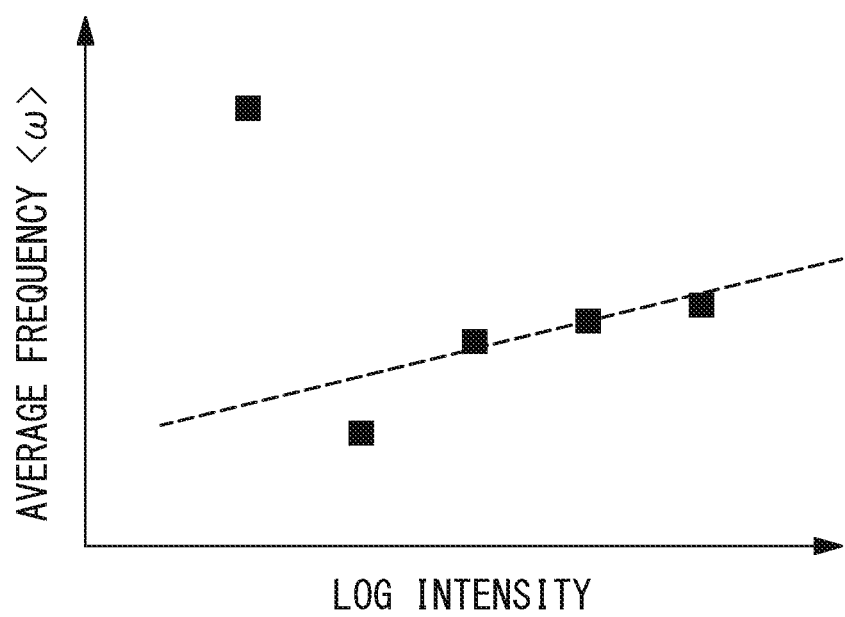
FIG. 3C is a graph showing the relationship between average frequencies (vertical axis) calculated in an integration interval including a high-frequency range and the intensities (horizontal axis) of the real-time Doppler spectra at the average frequencies.

FIGS. 3A and 3C show the relationship between the average frequencies<ω> and intensities (log) of the real-time Doppler spectra Freal (ω) at the average frequencies<ω>. FIG. 3A shows the case in which the integration interval is $0 \leq \omega \leq \omega_U$, and FIG. 3C shows the case in which the integration interval includes the high-frequency range in which the spectral intensities are at the background level. As shown in FIG. 3C, in the case in which the integration interval also includes the high-frequency range, the average frequencies<ω> become variable, in particular, when the spectral intensities are low, and the relationship between the average frequencies<ω> and the intensities does not become constant. In contrast, as shown in FIG. 3A, in the case in which integration interval is restricted to the range $0 \leq \omega \leq \omega_U$, the variation in the average frequencies<ω> is suppressed, and, as a result, average frequencies<ω> that linearly increase with respect to the intensities (log) are calculated.

Figure 4:
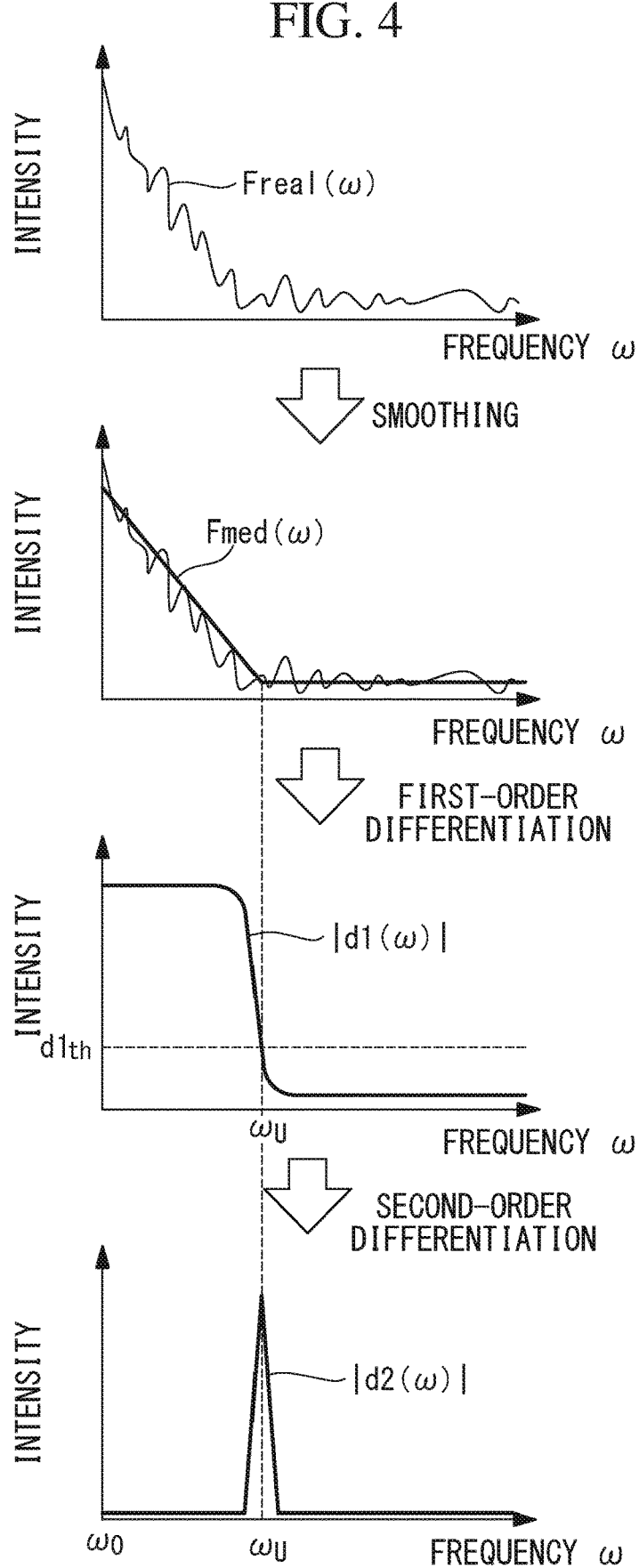
FIG. 4 is a diagram for explaining an example of an integration-interval setting step.

FIG. 4 shows an example of a method for setting the integration interval.

As shown in FIG. 4, a real-time Doppler spectrum Freal (ω) is smoothed by using a moving average filter, a median filter, or the like (smoothing step). Next, as a result of subjecting a smoothed real-time Doppler spectrum Fmed (ω) to first-order differentiation first-order differentiation with respect to the frequency ω, a first-order differential spectrum|d1(ω)| that represents the slopes of spectral intensities at the respective frequencies ω is obtained (first-order differentiating step). Next, the lower end of the integration interval is set to zero, and a frequency $\omega_U$ at which the intensity of the first-order differential spectrum|d1(ω)| becomes equal to a prescribed value $d1_{th}$ is set for the upper end of the integration interval.

Alternatively, a second-order differential spectrum|d2 (ω)| may be obtained by additionally differentiating the first-order differential spectrum|d1 (ω)| with respect to the frequency ω (second-order differentiation), and a frequency $\omega_U$ that gives a maximum value of a second-order differential spectrum|d2 (ω)| may be set for the upper end of the integration interval (second-order differentiating step).

In this way, as a result of using the differential spectrum|d1 (ω)| or |d2 (ω)|, it is possible to detect, by means of calculation, the frequency $\omega_U$, which is a boundary between the interval in which the real-time Doppler spectrum Freal (ω) is decaying and the interval in which the real-time Doppler spectrum Freal (ω) does not decay any further and the intensities thereof have become the lowest. Note that, in the example in FIG. 4, spectral intensities expressed as logarithms may be used.

Figure 5A:
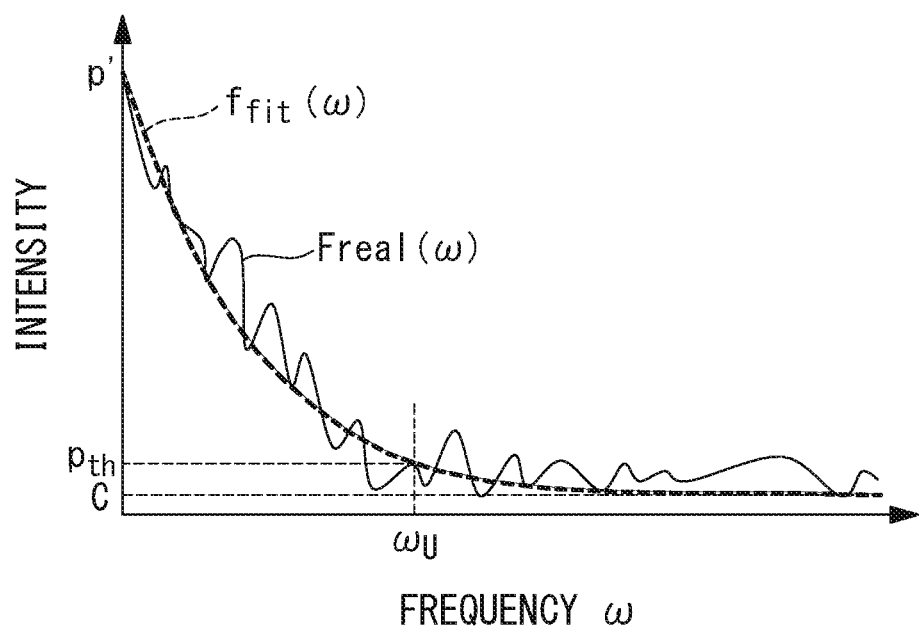
FIG. 5A is a diagram for explaining another example of the integration-interval setting step.

FIG. 5A shows another example of the method for setting the integration interval.

As shown in FIG. 5A, a real-time Doppler spectrum Freal (ω) is fitted by using an exponential function (fitting function) $f_{fit}(\omega)$ represented by the equation below (fitting step), and a frequency $\omega_U$ that satisfies $f_{fit}(\omega)=p_{th}$ is set for the upper end of the integration interval. The peak intensity p' of the exponential function $f_{fit}(\omega)$ is A+C.

$$f_{fit}(\omega)=A \times \exp(-\omega/B)+C$$

$p_{th}$ is set, for example, on the basis of the equation below:

$$p_{th}=(A+C) \times p_{fac}+C,$$

where $p_{fac}=0.001$.

Figure 5B:
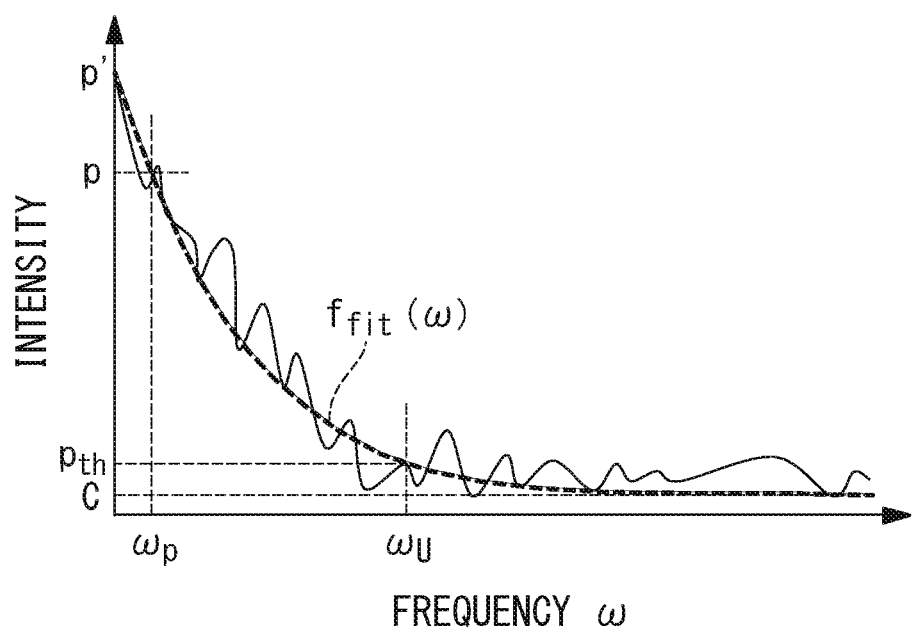
FIG. 5B is a diagram for explaining another example of the integration-interval setting step.

As shown in FIG. 5B, $p_{th}$ may be set on the basis of the equation below:

$$p_{th}=(f_{fit}(\omega_p)+C) \times p_{fac}+C,$$

where $p_{fac}=0.001$.

In other words, as a frequency $\omega_p$ that defines the peak intensity of the exponential function $f_{fit}(\omega)$, a frequency other than zero may be set in advance, and $f_{fit}(\omega_p)$ may be used instead of p'.

The average-frequency correcting portion 12 converts the average frequencies<ω> to corrected average frequencies<ω>$_{cal}$ by using a conversion equation G (F) and transmits the corrected average frequencies<ω>$_{cal}$ to the blood-vessel determining portion 13. The conversion equation G (F) is an equation in which the peak intensity p and the average frequency<ω> of a real-time Doppler spectrum Freal (ω) are variables, as represented in the equation below. In the equation below, F=<ω>, p is the intensity at a peak frequency $\omega_p$ defined in advance, and a1, a2, a3, b1, and b2 are correction factors that are experimentally determined.

$$G(F)=a(F) \times p+b(F)$$

$$a(F)=a1 \times F^2+a2 \times F+a3$$

$$b(F)=b1 \times F+b2$$

The conversion equation G (F): is a linear function of the peak intensity p, which has a slope a (F) and an intercept b (F) that are determined by an average frequency F; increases the average frequency F by a greater increment with a decrease in the peak intensity p; and increases the average frequency F by a smaller increment with an increase in the peak intensity p. By using such a conversion equation G (F), the average frequency F is corrected so as to reach substantially the same level as that of the average frequency<ω> when the peak intensity p is high, as shown in FIGS. 3A and 3B. Preferably, the correction factors a1, a2, a3, b1, and b2 of the conversion equation G (F) are determined so that the corrected average frequencies<ω>$_{cal}$ are constant regardless of the peak intensities p, as shown in FIG. 3B. By doing so, corrected average frequencies<ω>$_{cal}$ that have a one-to-one correspondence with the blood-flow velocities are obtained regardless of the peak intensities p of the real-time Doppler spectra Freal (ω).

Figure 6A:
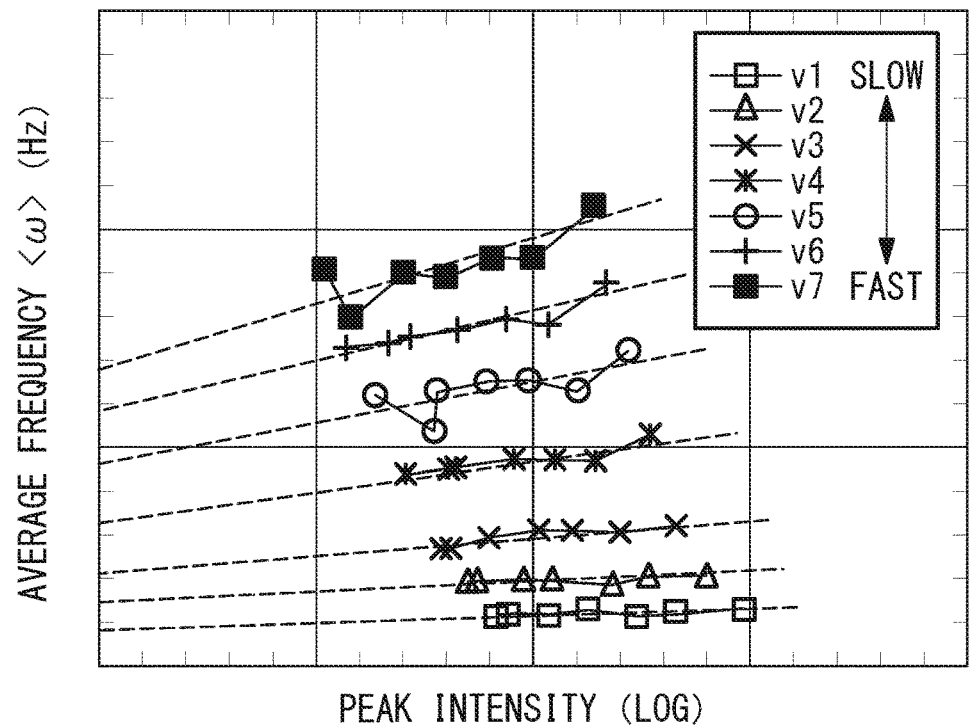
FIG. 6A is a graph showing the relationship between peak intensities of the real-time Doppler spectra of small blood vessels and the average frequencies.
Figure 7A:
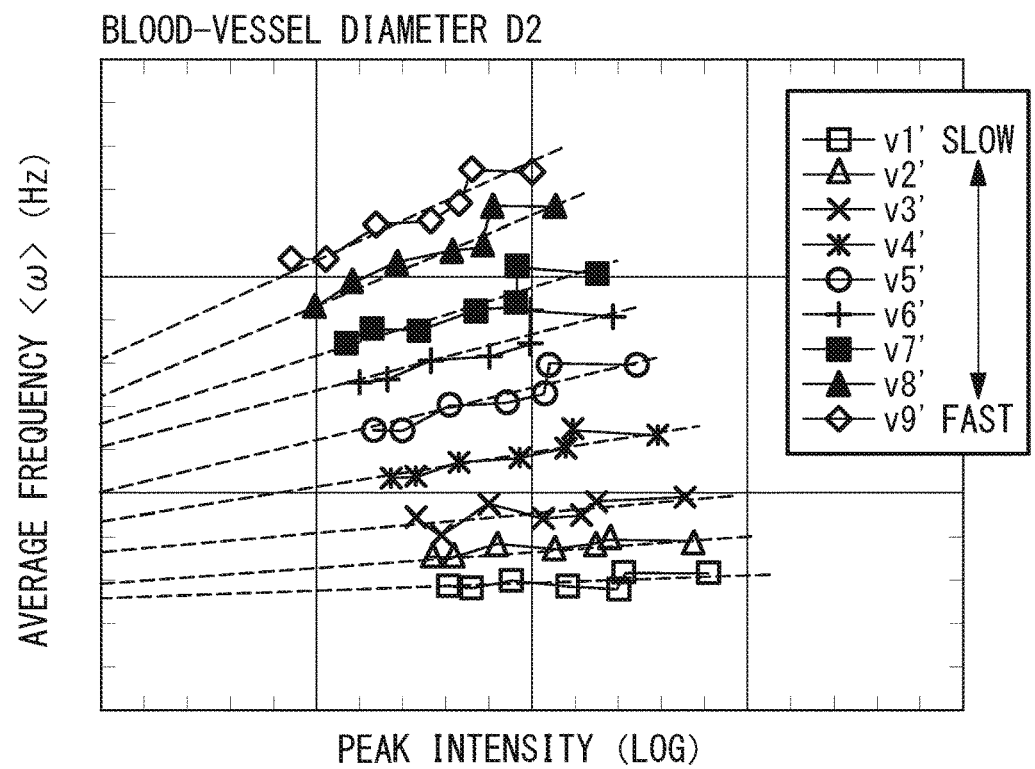
FIG. 7A is a graph showing the relationship between peak intensities of the real-time Doppler spectra of large blood vessels and the average frequencies.

FIGS. 6A and 7A individually show the relationship between the peak intensities p and the average frequencies<ω> of the real-time Doppler spectra Freal (ω) for small blood vessels (blood-vessel diameter D1) and large blood vessels (blood-vessel diameter D2, where D1<D2). At individual blood-flow velocities v1 to v7 and v1' to v9', with an increase in the peak intensities p, the average frequencies<ω> also increase. In other words, because the average frequencies<ω> differ in accordance with the peak intensities p even if the blood-flow velocities are the same, it is difficult to determine the blood-flow velocities and the sizes of the blood vessels only on the basis of the average frequencies<ω>.

Here, the peak intensities p and the average frequencies<ω> at the respective blood-flow velocities have a linear relationship, as indicated by broken lines in FIGS. 6A and 7A, and, at all of the blood-flow velocities, the slopes and the intercepts show increasing trends with an increase in the average frequencies<ω>. At the respective blood-flow velocities, the reliability of the average frequencies<ω> increases with an increase in the peak intensities p. Therefore, by correcting the average frequencies<ω> so as to reach the same levels as those of the average frequencies<ω> when the peak intensities p are high, it is possible to obtain corrected average frequencies<ω>$_{cal}$ that accurately correspond to the blood-flow velocities.

Figure 6B:
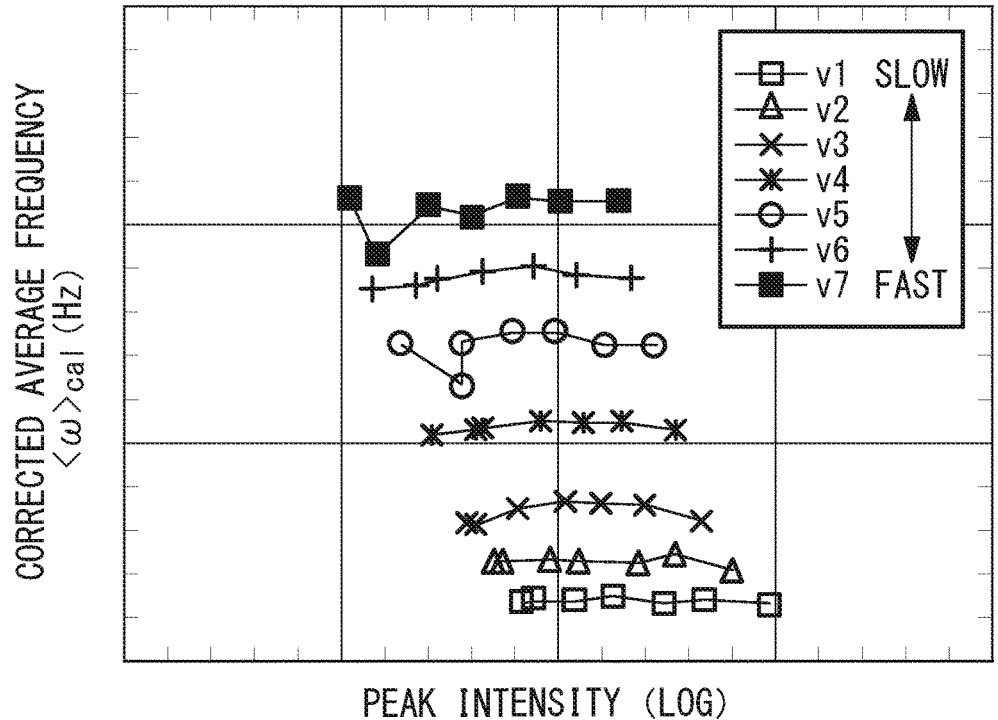
FIG. 6B is a graph showing the result of converting the average frequencies in FIG. 6A by using a conversion equation.
Figure 7B:
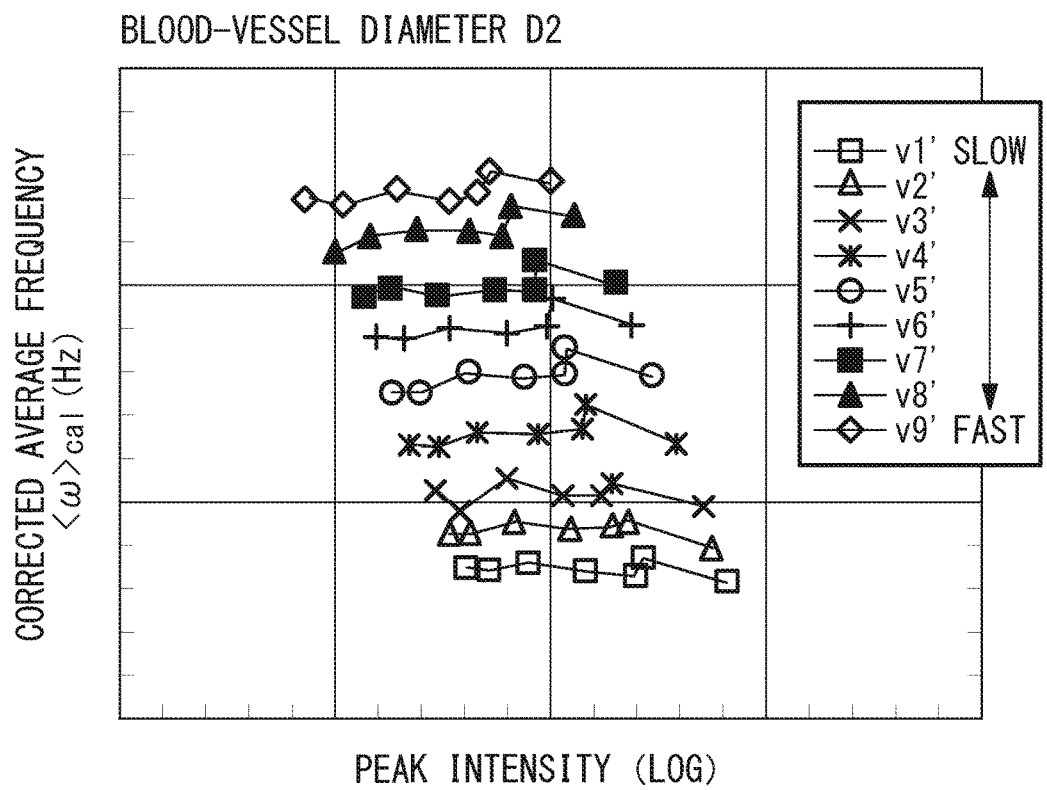
FIG. 7B is a graph showing the result of converting the average frequencies in FIG. 7A by using the conversion equation.

FIGS. 6B and 7B individually show the corrected average frequencies<ω>$_{cal}$ obtained by converting the average frequencies<ω> in FIGS. 6A and 7A by using the conversion equation G (F).

The correction factors a1, a2, a3, b1, and b2 of the conversion equation G (F) used in calculating the corrected average frequencies<ω>$_{cal}$ in FIG. 6B are as follows:

$a1=-4.45E-07;$ $a2=2.21E-05;$ $a3=-7.47E-01;$ $b1=1.21E+00;$ and $b2=1.22E+00.$ The correction factors a1, a2, a3, b1, and b2 of the conversion equation G (F) used in calculating the corrected average frequencies<ω><$_{cal}$ in FIG. 7B are as follows:

$a1=-1.17E-06;$ $a2=2.21E-05;$ $a3=-7.47E-01;$ $b1=1.27E+00;$ and $b2=1.22E+00.$ The above-described correction factors a1, a2, a3, b1, and b2 are values optimized by using actually measured values of the peak intensities p and the average frequencies<ω> in FIGS. 6A and 7A. In this way, the correction factors a1, a2, a3, b1, and b2 that are optimum with respect to the small blood vessels having the blood-vessel diameter D1 and the correction factors a1, a2, a3, b1, and b2 that are optimum with respect to the thick blood vessels having the blood-vessel diameter D2 are substantially identical to each other. In other words, by optimizing the correction factors a1, a2, a3, b1, and b2, it is possible to correct the average frequencies<ω> by using the common conversion equation G (F) regardless of the blood-vessel diameters.

The blood-vessel determining portion 13 compares the corrected average frequencies<ω>$_{cal}$ received from the average-frequency correcting portion 12 with a prescribed threshold. The prescribed threshold is an average frequency that corresponds to a minimum value of the diameters of the large blood vessels B2 that serve as detection targets, and is set by, for example, the surgeon via an input means (not shown). The blood-vessel determining portion 13 determines that the large blood vessels B2 are present when the corrected average frequencies<ω>$_{cal}$ are equal to or greater than the threshold, and outputs TRUE signals to the control portion 14. On the other hand, the blood-vessel determining portion 13 determines that the large blood vessels B2 are not present in regions irradiated with the laser light L when the corrected average frequencies<ω>$_{cal}$ are less than the threshold, and outputs FALSE signals to the control portion 14.

The control portion 14 causes the visible light source 9 to output the visible light V when the TRUE signals are received from the blood-vessel determining portion 13, and causes the visible light source 9 to stop outputting the visible light V when the FALSE signals are received from the blood-vessel determining portion 13. By doing so, the visible light V is radiated only onto positions at which the large blood vessels B2 are detected.

Figure 8:
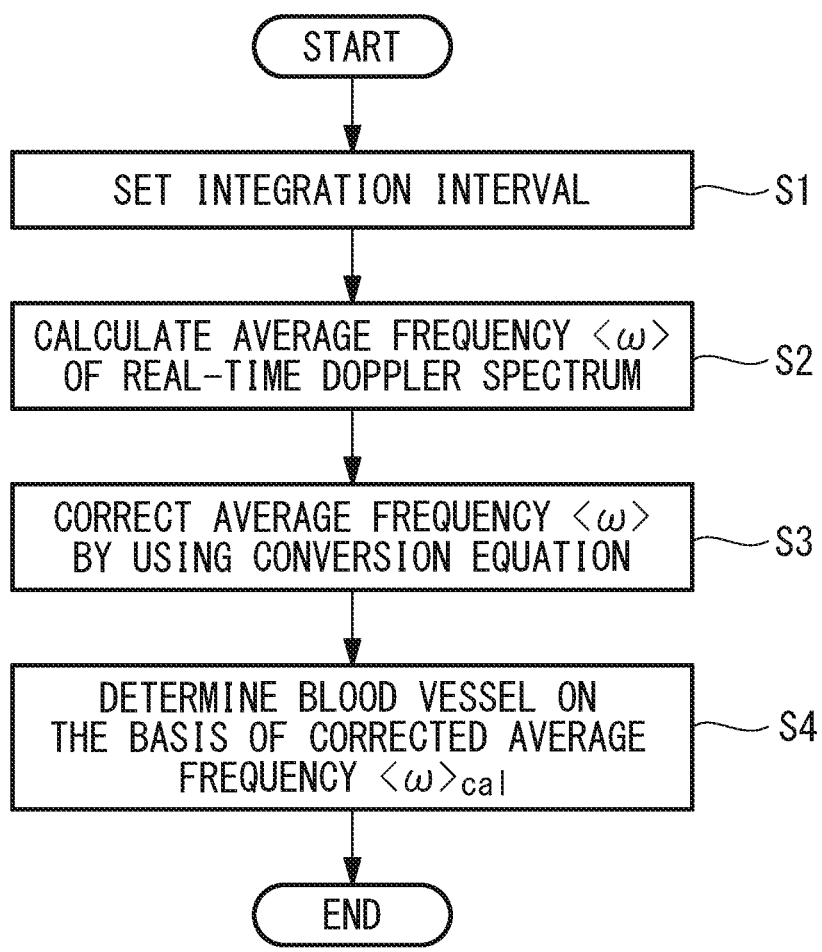
FIG. 8 is a flowchart for explaining a blood-vessel recognizing method employing the blood-vessel recognizing device in FIG. 1.

Next, the operation of the blood-vessel recognizing device 100, thus configured, will be described with reference to FIG. 8.

The blood-vessel recognizing device 100 according to this embodiment is used together with an endoscope for observing the interior of a living organism. First, the endoscope and the probe 1 of the blood-vessel recognizing device 100 are inserted into a body.

Next, outputting of the laser light L from the laser light source 8 is started, and the probe 1 is moved so that the laser light L radiated from the irradiation optical fiber 6 is scanned on the surface of the tissue T while the surface of the tissue T is observed with the endoscope.

The scattered light S generated in the regions irradiated with the laser light L is received by the light-receiving optical fiber 7 and is detected by the light-detecting portion 3. Then, time waveform data of the intensities of the scattered light S are generated in the storage portion 10.

Next, the time waveform data are read out into the analyzing portion 11 from the storage portion 10, and the real-time Doppler spectra Freal (ω) are calculated from the time waveform data in the analyzing portion 11. Next, in the analyzing portion 11, the integration interval $0 \leq \omega \leq \omega_U$ is set on the basis of the shapes of the real-time Doppler spectra Freal (ω), as shown in FIG. 8 (integration-interval setting step S1), and the average frequencies<ω> in the integration interval $0 \leq \omega \leq \omega_U$ are calculated (average-frequency calculating step S2).

Next, in the average-frequency correcting portion 12, the average frequencies<ω> are converted to the corrected average frequencies<ω>$_{cal}$ in accordance with the conversion equation G (F) (average-frequency correcting step S3).

Next, in the blood-vessel determining portion 13, on the basis of the corrected average frequencies<ω>$_{cal}$, it is determined whether or not the large blood vessels B2 are present in the regions irradiated with the laser light L (S4). When the corrected average frequencies<ω>$_{cal}$ are equal to or greater than the threshold, the TRUE signals are output to the control portion 14 from the blood-vessel determining portion 13. On the other hand, when the corrected average frequencies<ω>$_{cal}$ are less than the threshold, the FALSE signals are output to the control portion 14 from the blood-vessel determining portion 13.

When the TRUE signals are received from the blood-vessel determining portion 13, the control portion 14 causes the visible light V to be emitted from the irradiation optical fiber 6 together with the laser light L. On the other hand, when the FALSE signals are received from the blood-vessel determining portion 13, the control portion 14 does not cause the visible light V to be emitted. Therefore, it is possible for the surgeon to recognize the regions irradiated with the visible light V as regions in which the large blood vessels B2 are present.

As has been described above, the intensities of the real-time Doppler spectra Freal(ω) differ in accordance with the environment in which the blood vessels B1 and B2 are placed, such as the depths of the blood vessels B1 and B2 in the tissue T and properties of the tissue T, even if the blood-flow velocities of the blood vessels B1 and B2 are the same, and thus, variation due to the difference in the spectral intensities occurs in the average frequencies<ω>. Therefore, in the case in which the sizes of the blood vessels B1 and B2 are determined only on the basis of the average frequencies<ω>, the presence of the large blood vessels B2 may not be determined accurately as result of, for example, low average frequencies<ω> being calculated despite the presence of the large blood vessels B2 at a deep position.

In contrast, with this embodiment, by correcting the variation in the average frequencies<ω> on the basis of the peak intensities p (or p') of the real-time Doppler spectra Freal(ω), the corrected average frequencies<ω>$_{cal}$ that accurately correspond to the blood-flow velocities are obtained. It is possible to accurately recognize the sizes of the blood vessels B1 and B2 on the basis of such corrected average frequencies<ω>$_{cal}$, and thus, there is an advantage in that it is possible to allow the surgeon to recognize the positions of the large blood vessels B2 in a reliable manner.

In addition, by separately setting, on the basis of the shapes of the real-time Doppler spectra Freal (ω), the integration intervals for calculating the average frequencies<ω> of the real-time Doppler spectra Freal (ω), it is possible to enhance the calculation precision of the average frequencies<ω>, and thus, there is an advantage in that it is possible to further enhance the precision for determining the sizes of the blood vessels B1 and B2.

Figure 9:
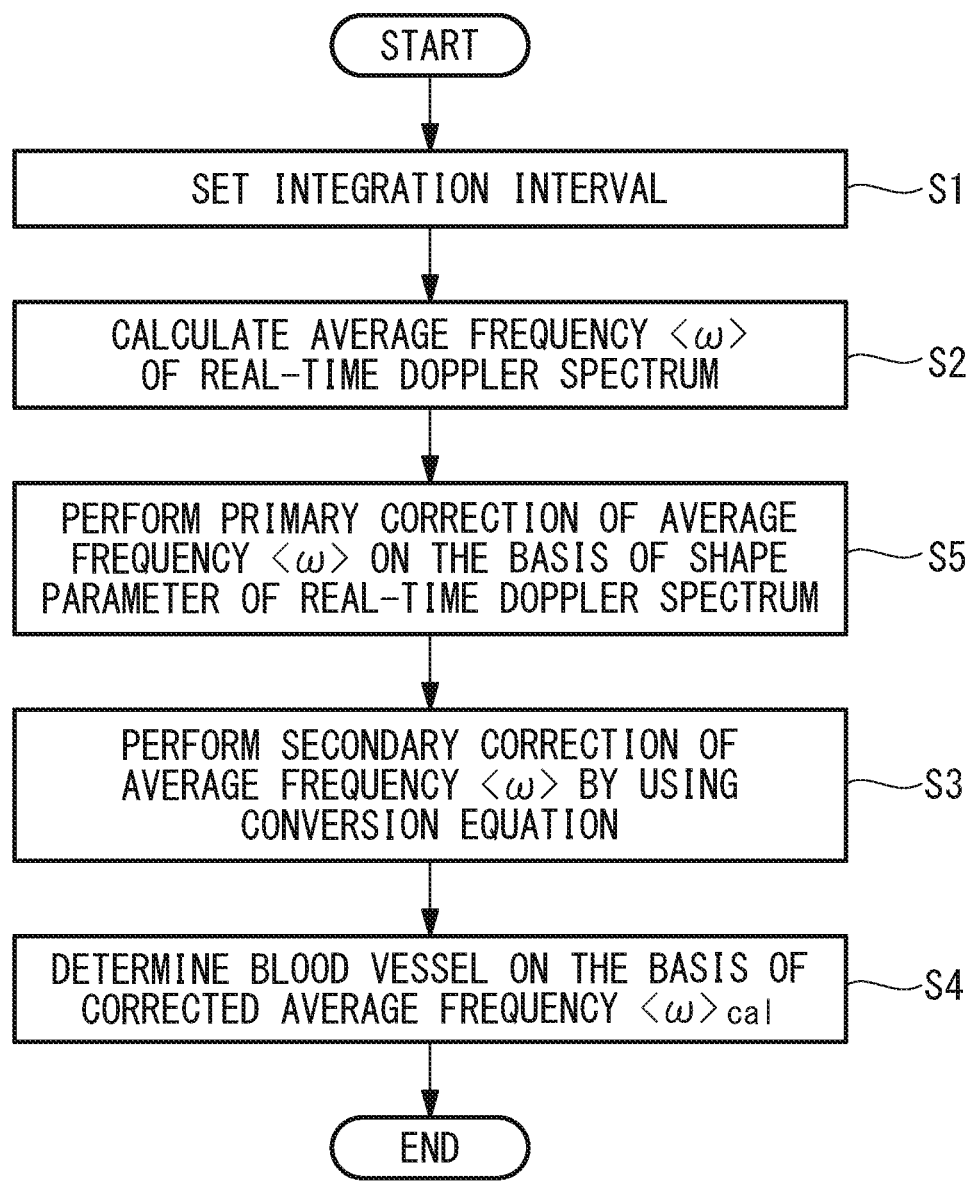
FIG. 9 is a flowchart for explaining a modification of the blood-vessel recognizing method employing the blood-vessel recognizing device in FIG. 1.

In this embodiment, although the average frequencies<ω> of the real-time Doppler spectra Freal (ω) are corrected in one step by using the conversion equation G (F), alternatively, the average frequencies<ω> may be corrected in two steps, as shown in FIG. 9. Specifically, before the correction by means of the conversion equation G (F), the average frequencies<ω> may be subjected to primary correction on the basis of the shapes of the real-time Doppler spectra Freal (ω) (S5), and the corrected average frequencies<ω>$_{cal1}$ that have been subjected to the primary correction may be subjected to secondary correction by using the conversion equation G (F).

Because the overall shapes of the real-time Doppler spectra Freal (ω) originating from the small blood vessels B1 are upward-convex decay curves, there is a tendency to calculate average frequencies<ω> that are greater than the average frequencies<ω> accurately corresponding to the blood-flow velocities. On the other hand, because the overall shapes of the real-time Doppler spectra Freal (ω) originating from the large blood vessels B2 are downward-convex decay curves, there is a tendency to calculate average frequencies<ω> that are less than the average frequencies<ω> accurately corresponding to the blood-flow velocities. Therefore, it is possible to correct the variation in the average frequencies<ω> caused by the blood-vessel diameters on the basis of a shape parameter m that indicates whether the decay curve representing the overall shape of a real-time Doppler spectrum Freal (ω) is upward convex or downward convex.

The shape parameter m is a parameter that increases when a real-time Doppler spectrum Freal (ω) is upward convex, and that decrease when a real-time Doppler spectrum Freal (ω) is downward convex.

Figure 10:
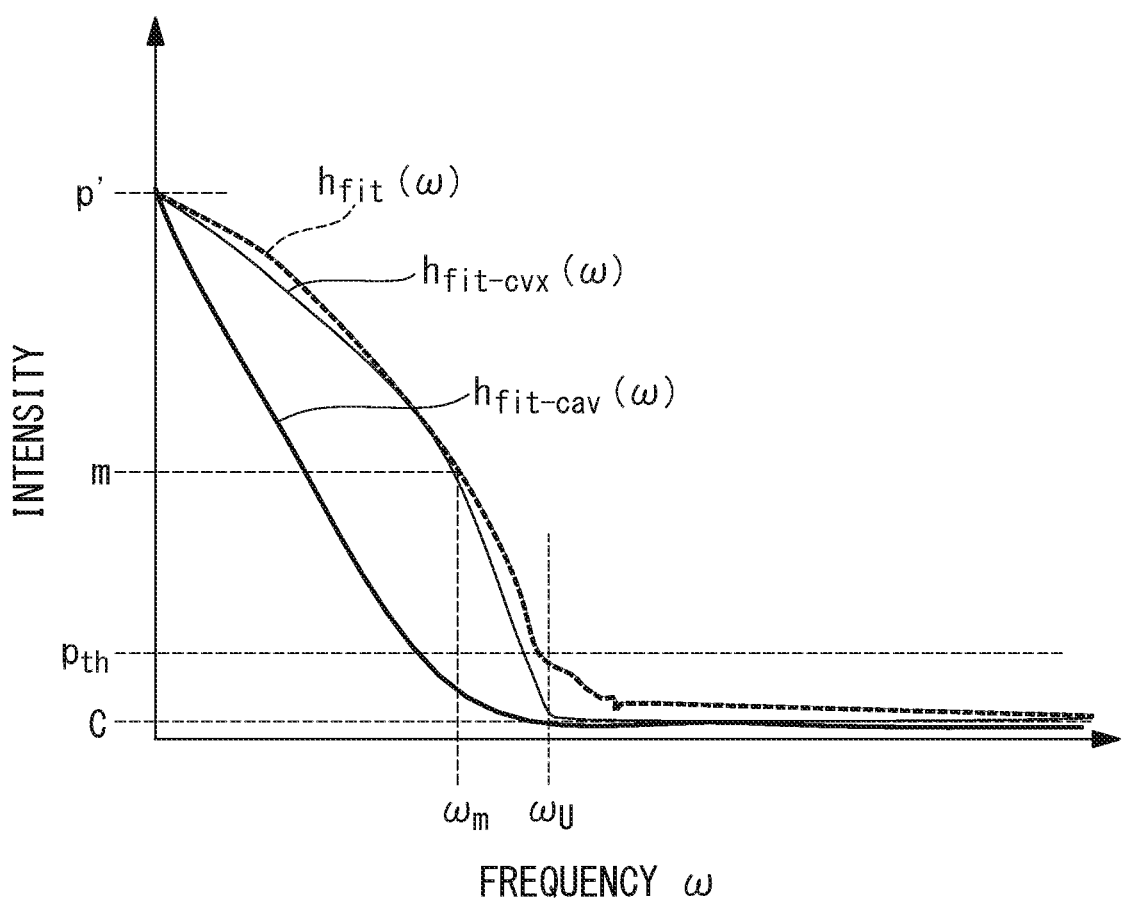
FIG. 10 is a diagram for explaining a method for calculating a shape parameter of the real-time Doppler spectra.

FIG. 10 shows an example of calculation of the shape parameter m.

As shown in FIG. 10, a real-time Doppler spectrum Freal (ω) is fitted by using a fitting function $h_{fit}(\omega)$ below, and thus, coefficients A and B are calculated:

$$h_{fit}(\omega) = A \times h_{fit\text{-}cvx}(\omega) + B \times h_{fit\text{-}cav}(\omega) + C,$$

where $h_{fit\text{-}cvx}(\omega)$ is a normalized upward-convex function, $h_{fit\text{-}cav}(\omega)$ is a normalized downward-convex function, and C is a constant.

When the blood vessels are small, the coefficient A increases, and the coefficient B decreases. On the other hand, when the blood vessels are large, the coefficient A decreases, and the coefficient B increases. The parameter m is a value that varies in a range of values that are equal to or greater than the constant C and equal to or less than the peak intensity p'. The relationship between the coefficients A and B and the shape parameter m is set so that the shape parameter m increases with an increase in the coefficient A or with a decrease in the coefficient B.

Figure 11A:
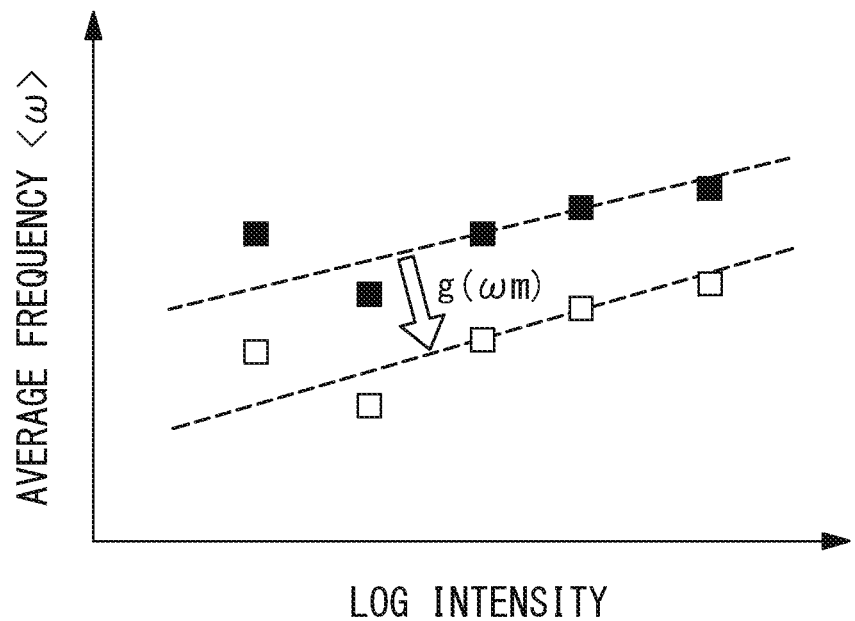
FIG. 11A is a diagram for explaining a primary correction of the average frequencies, performed by means of a conversion function in the case of the real-time Doppler spectra of the small blood vessels.
Figure 11B:
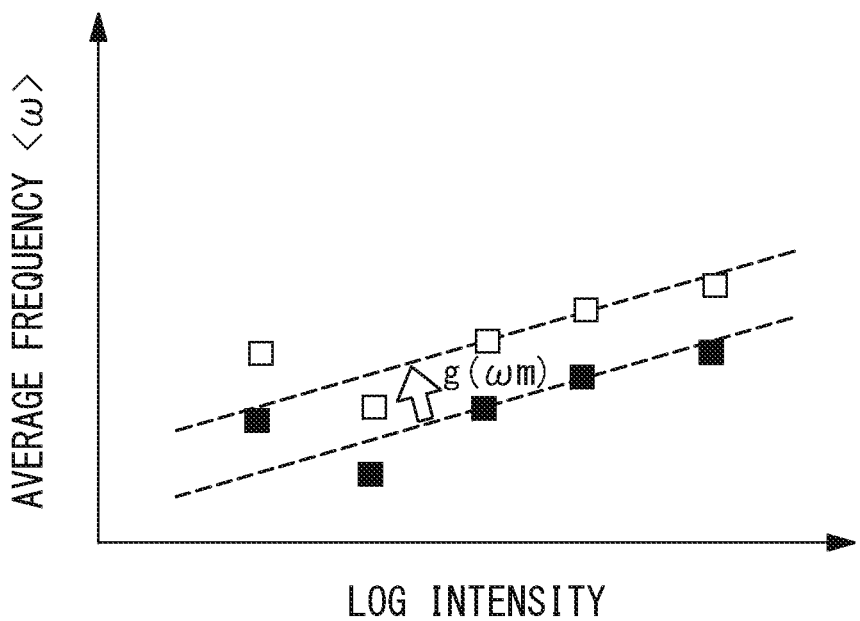
FIG. 11B is a diagram for explaining a primary correction of the average frequencies, performed by means of the conversion function in the case of the real-time Doppler spectra of the large blood vessels.

Next, as shown in FIGS. 11A and 11B, the average frequencies<ω> are corrected by using a conversion function g ($\omega_m$) on the basis of the frequencies $\omega_m$ at which the shape parameter m is applied. The conversion function g ($\omega_m$) is set so as to convert a straight line representing the relationship between the peak intensities p and the average frequencies<ω> to an ideal straight line. Therefore, the average frequencies<ω> of the real-time Doppler spectra Freal (ω) of the small blood vessels are corrected to lower values by means of the conversion function g ($\omega_m$), as shown in FIG. 11A. On the other hand, the average frequencies<ω> of the real-time Doppler spectra Freal (ω) of the large blood vessels are corrected to greater values by means of the conversion function g ($\omega_m$), as shown in FIG. 11B.

As has been described above, as a result of subjecting the variation in the average frequencies<ω> caused by the blood-vessel diameters to primary correction on the basis of the shape parameter m of the real-time Doppler spectra Freal (ω) and subjecting the corrected average frequencies<ω>$_{cal1}$ that have been subjected to the primary correction to secondary correction by using the conversion equation G (F), corrected average frequencies<ω>$_{cal2}$ that more accurately correspond to the blood-flow velocities are obtained. Therefore, it is possible to more accurately determine the sizes of blood vessels on the basis of the corrected average frequencies<ω>$_{cal2}$.

As shown in FIG. 10, the shape parameter m may be a central value between the peak intensity p' and the background level C of the fitting function $h_{fit}(\omega)$. Alternatively, the shape parameter m may be a central value between the peak intensity p' and a prescribed intensity $p_{th}$. In calculating the shape parameter m, the peak intensity p of a real-time Doppler spectrum Freal (ω) may be used instead of the peak intensity p'.

The above-described embodiment also leads to the following aspects.

A first aspect of the present invention is a blood-vessel recognizing method for recognizing blood vessels present in biological tissue on the basis of real-time Doppler spectra obtained by applying Fourier transformation to time waveforms of intensities of scattered light generated in the biological tissue due to irradiation with laser light, the method including: an average-frequency calculating step of calculating average frequencies of the real-time Doppler spectra; and an average-frequency correcting step of correcting the average frequencies calculated in the average-frequency calculating step on the basis of peak intensities of the real-time Doppler spectra.

With this aspect, the real-time Doppler spectra based on the scattered light generated in the blood vessels in the biological tissue due to irradiation with the laser light exhibit intensities at frequencies in accordance with the blood velocities (blood-flow velocities) of blood flowing in the blood vessels. The blood-flow velocities are correlated with the sizes of the blood vessels. Therefore, it is possible to recognize the sizes of the blood vessels present in the regions irradiated with the laser light on the basis of the average frequencies of the real-time Doppler spectra calculated in the average-frequency calculating step.

In this case, the intensities of the real-time Doppler spectra change as a whole in accordance with the environment in which the blood vessels are placed (for example, the depths of blood vessels in biological tissue and the properties of biological tissue). Therefore, the average frequencies calculated from the real-time Doppler spectra exhibit variation in accordance with the environment in which the blood vessels are placed even if the blood-flow velocities are the same. In the average-frequency correcting step, the variation in the average frequencies is corrected on the basis of the peak intensities of the real-time Doppler spectra. It is possible to accurately recognize the sizes of the blood vessels on the basis of the average frequencies that has been corrected in this way, regardless of the environment in which the blood vessels are placed.

In the above-described aspect, in the average-frequency correcting step, the average frequencies may be corrected by using a conversion equation that uses the average frequencies and the peak intensities as variables, and that increases the average frequencies with a greater increment as the peak intensities decrease. The conversion equation may correct the average frequencies so that the corrected average frequencies become constant regardless of the peak intensities.

The average frequencies of the real-time Doppler spectra decrease as the peak intensities decrease. Therefore, as a result of correcting the average frequencies with a greater increment as the peak intensities decrease by using the conversion equation, it is possible to more accurately correct a decrease in the average frequencies caused by a decrease in the intensities of the real-time Doppler spectra.

In the above-described aspect may include an integration-interval setting step of setting an integration interval for calculating the average frequencies on the basis of the intensities of the real-time Doppler spectra.

In the real-time Doppler spectra, a high-frequency range having low intensities is a cause of deterioration of calculation precision of the average frequencies. By setting the integration interval so as to exclude such a high-frequency range, it is possible to enhance the calculation precision of the average frequencies.

In the above-described aspect, the integration-interval setting step may include a smoothing step of applying smoothing processing to the real-time Doppler spectra.

The real-time Doppler spectra include numerous small peaks. By using real-time Doppler spectra in which such numerous small peaks are smoothed by means of the smoothing processing, it is possible to further enhance the calculation precision of the average frequencies.

In the above-described aspect, the integration-interval setting step may include a first-order differentiating step of performing, with respect to frequency, first-order differentiation of the real-time Doppler spectra that have been subjected to the smoothing processing in the smoothing step.

By doing so, it is possible to more accurately distinguish, on the basis of the intensities of a first-order differential spectrum of the real-time Doppler spectra, an interval in which the real-time Doppler spectra are significantly decaying and an interval in which the intensities of the real-time Doppler spectra have become the lowest, and thus, it is possible to set an integration interval that is more appropriate for calculating the average frequencies.

In the above-described aspect, the integration-interval setting step may include a second-order differentiating step of performing, with respect to frequency, second-order differentiation of the real-time Doppler spectra that have been subjected to the smoothing processing in the smoothing step.

By doing so, it is possible to more accurately identify, on the basis of the intensities of a second-order differential spectrum of the real-time Doppler spectra, a boundary between the interval in which the real-time Doppler spectra are significantly decaying and the interval in which the intensities of the real-time Doppler spectra have become the lowest, and thus, it is possible to set an integration interval that is more appropriate for calculating the average frequencies.

In the above-described aspect, the integration-interval setting step may include a fitting step of calculating a fitting function of the real-time Doppler spectra.

By doing so, it is possible to more appropriately set the integration interval by using the fitting function.

In the above-described aspect, in the average-frequency correcting step, the average frequencies may be corrected on the basis of a shape parameter that indicates whether overall shapes of the real-time Doppler spectra are upward convex or downward convex.

Because the real-time Doppler spectra of small blood vessels are upward-convex decay curves as a whole, there is a tendency to calculate the average frequencies that take greater values. On the other hand, because the real-time Doppler spectra of large blood vessels are downward-convex decay curves as a whole, there is a tendency to calculate the average frequencies that take lower values. Therefore, by taking the shape parameter into consideration in addition to the peak intensities, it is possible to also correct the variation in the average frequencies caused by differences in the blood-vessel diameters.

A second aspect of the present invention is a blood-vessel recognizing device including: a laser-light radiating portion that radiates laser light onto biological tissue; a spectrum acquisition portion that acquires time waveforms of intensities of scattered light generated in the biological tissue due to the irradiation with the laser light, and that acquires real-time Doppler spectra by applying Fourier transformation to the acquired time waveforms; an average-frequency calculating portion that calculates average frequencies of the real-time Doppler spectra acquired by the spectrum acquisition portion; and an average-frequency correcting portion that corrects the average frequencies calculated by the average-frequency calculating portion on the basis of peak intensities of the real-time Doppler spectra.

In the above-described second aspect may include a blood-vessel determining portion that determines the sizes of blood vessels on the basis of the average frequencies corrected by the average-frequency correcting portion.

REFERENCE SIGNS LIST 100 blood-vessel recognizing device
1 probe
2 light-source unit
3 light-detecting portion
4 control device
5 probe body
6 irradiation optical fiber (laser-light radiating portion)
7 light-receiving optical fiber (spectrum acquisition portion)
8 laser light source
9 visible light source
10 storage portion (spectrum acquisition portion)
11 analyzing portion (average-frequency calculating portion)
12 average-frequency correcting portion
13 blood-vessel determining portion
14 control portion
S1 integration-interval setting step
S2 average-frequency calculating step
S3 average-frequency correcting step
T tissue
B1, B2 blood vessel

The invention claimed is:

1. A blood-vessel recognizing method for recognizing blood vessels present in biological tissue, the method comprising:
　obtaining real-time Doppler spectra on the basis of time waveforms data of intensities of scattered light generated in the biological tissue due to irradiation with laser light;
　calculating average frequencies of the real-time Doppler spectra;
　correcting the calculated average frequencies by using a conversion equation that uses the average frequencies and peak intensities of the real-time Doppler spectra as variables, and that increases the average frequencies with a greater increment as the peak intensities decrease; and
　determining whether or not blood vessels are present in regions of the biological tissue irradiated with the laser light on the basis of the corrected average frequencies.

2. The blood-vessel recognizing method according to claim 1, wherein, in the determining, it is determined whether or not blood vessels having diameters to be detected are present on the basis of a result of comparison between the corrected average frequencies and a threshold.

3. The blood-vessel recognizing method according to claim 2, wherein the threshold is an average frequency that corresponds to a minimum value of the diameters to be detected.

4. The blood-vessel recognizing method according to claim 1, wherein the conversion equation corrects the average frequencies so that the corrected average frequencies become constant regardless of the peak intensities.

5. The blood-vessel recognizing method according to claim 1, further comprising:
　setting an integration interval for calculating the average frequencies on the basis of the intensities of the real-time Doppler spectra.

6. The blood-vessel recognizing method according to claim 5, wherein the setting includes applying smoothing processing to the real-time Doppler spectra.

7. The blood-vessel recognizing method according to claim 6, wherein the setting includes performing, with respect to frequency, first-order differentiation of the real-time Doppler spectra that have been subjected to the smoothing processing.

8. The blood-vessel recognizing method according to claim 6, wherein the setting includes performing, with respect to frequency, second-order differentiation of the real-time Doppler spectra that have been subjected to the smoothing processing.

9. The blood-vessel recognizing method according to claim 5, wherein the setting includes calculating a fitting function of the real-time Doppler spectra.

10. A blood-vessel recognizing method for recognizing blood vessels present in biological tissue, the method comprising:
　obtaining real-time Doppler spectra on the basis of time waveforms data of intensities of scattered light generated in the biological tissue due to irradiation with laser light;
　calculating average frequencies of the real-time Doppler spectra;
　correcting the calculated average frequencies on the basis of a shape parameter that indicates whether overall shapes of the real-time Doppler spectra are upward convex or downward convex; and
　determining whether or not blood vessels are present in regions of the biological tissue irradiated with the laser light on the basis of the corrected average frequencies.

* * * * *